United States Patent
Tian et al.

(10) Patent No.: US 9,377,287 B2
(45) Date of Patent: Jun. 28, 2016

(54) EDDY CURRENT BASED METHOD FOR COATING THICKNESS MEASUREMENT

(75) Inventors: Yong Tian, Peoria, IL (US); Douglas Alexander Rebinsky, Peoria, IL (US); Christopher Anthony Kinney, Iuka, MS (US); Kegan Luick, Corinth, MS (US)

(73) Assignee: Caterpillar Inc., Peoria, IL (US)

( * ) Notice: Subject to any disclaimer, the term of this patent is extended or adjusted under 35 U.S.C. 154(b) by 1043 days.

(21) Appl. No.: 13/298,887

(22) Filed: Nov. 17, 2011

(65) Prior Publication Data
US 2013/0132012 A1    May 23, 2013

(51) Int. Cl.
| | | |
|---|---|---|
| *G01R 1/20* | (2006.01) | |
| *G01R 1/40* | (2006.01) | |
| *G01C 7/00* | (2006.01) | |
| *G01C 7/02* | (2006.01) | |
| *G01B 7/06* | (2006.01) | |
| *G01N 27/90* | (2006.01) | |
| *G01B 7/00* | (2006.01) | |

(52) U.S. Cl.
CPC ............ *G01B 7/105* (2013.01); *G01N 27/9086* (2013.01); *G01B 7/00* (2013.01)

(58) Field of Classification Search
CPC ........................................................ G01B 7/00
USPC .............. 702/58, 65, 82, 104, 108, 150, 183; 222/52
See application file for complete search history.

(56) References Cited

U.S. PATENT DOCUMENTS

| | | | |
|---|---|---|---|
| 5,963,031 A | 10/1999 | de Halleux et al. | |
| 6,602,724 B2 | 8/2003 | Redeker et al. | |
| 6,715,640 B2 * | 4/2004 | Tapphorn et al. | ............... 222/52 |
| 6,762,604 B2 | 7/2004 | Le | |
| 6,806,703 B2 * | 10/2004 | Le Bihan et al. | ............. 324/229 |
| 6,815,947 B2 | 11/2004 | Scheiner et al. | |

(Continued)

FOREIGN PATENT DOCUMENTS

| | | |
|---|---|---|
| JP | 2007-263981 A | 10/2007 |
| KR | 10-2011-0079862 A | 7/2011 |

OTHER PUBLICATIONS

Hagemaier, D.J.; "Eddy current impedance plane analysis, Materials Evaluation," 41 (1983) 211-218—abstract.

(Continued)

*Primary Examiner* — Gregory J Toatley
*Assistant Examiner* — Felix Suarez
(74) *Attorney, Agent, or Firm* — Finnegan, Henderson, Farabow, Garrett & Dunner, LLP

(57) ABSTRACT

A method of configuring an eddy current detector to measure a thickness of a coating on a substrate includes measuring an impedance of the coated substrate, and establishing an impedance plane plot using a computer. The method may also include determining a rotation angle. The rotation angle may be an angle of rotation of the impedance plane plot that will make the inductive reactance component of the impedance substantially insensitive to substrate electrical conductivity within a coating thickness range. The method may further include establishing a calibration curve that is substantially insensitive to substrate electrical conductivity using the rotation angle. The calibration curve may be a curve that relates the inductive reactance component of the impedance to coating thickness.

22 Claims, 6 Drawing Sheets

(56) References Cited

U.S. PATENT DOCUMENTS

| | | |
|---|---|---|
| 6,878,036 B2 | 4/2005 | Hanawa et al. |
| 7,019,519 B2 | 3/2006 | Le |
| 7,714,572 B2 | 5/2010 | Tada et al. |
| 8,078,419 B2 * | 12/2011 | Kobayashi et al. ............ 702/64 |
| 2004/0138838 A1 | 7/2004 | Scheiner et al. |
| 2005/0017712 A1 | 1/2005 | Le |
| 2007/0077362 A1 | 4/2007 | Ruzzo et al. |

OTHER PUBLICATIONS

Moulder, J., Uzal, E., Rose, J.; "Thickness and conductivity of metallic layers from eddy current measurements," Rev. Sci. Instrum., 63 (1992) 3455-3465.

* cited by examiner

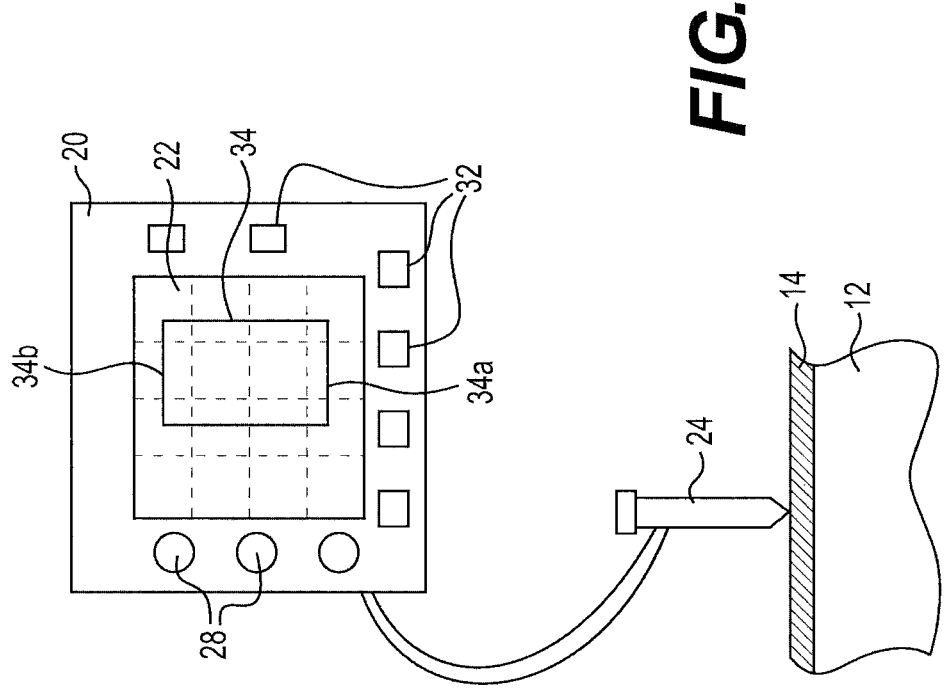

EDDY CURRENT BASED METHOD FOR COATING THICKNESS MEASUREMENT

TECHNICAL FIELD

The present disclosure relates generally to an eddy current based method of measuring the thickness of a coating.

BACKGROUND

Coating thickness is a variable that plays an important role in product quality, process control, and cost control. Measurement of coating thickness can be done with many different instruments. The issues that determine what method is best for a given coating measurement include the type of coating, the substrate material, the thickness range of the coating, the size and shape of the part, and the cost of the equipment. Nondestructive thickness testing methods such as ultrasonic pulse-echo techniques, magnetic pull-off or electromagnetic induction based techniques using magnetic film gages, and eddy current based techniques are commonly used to measure the thickness of coatings in the industry.

Eddy current based techniques are typically used to measure the thickness of nonconductive coatings on nonmagnetic and conductive substrates. A coil of fine wire conducting an alternating current is used to set up an alternating magnetic field at the surface of the instrument's probe. When the probe is brought in contact with the surface of the coating, the alternating magnetic field will set up eddy currents on the surface of the conductive substrate. The coating acts as a spacer between the probe and the conductive substrate. As the distance between the probe and the conductive base metal increases, the eddy current field strength decreases because less of the probe's magnetic field can interact with the base metal. Electrical impedance, which is the total opposition that a circuit presents to alternating current, is used as a measure of the eddy current field strength. Electrical impedance, which is measured in ohms, includes three components—resistance, inductive reactance, and capacitive reactance. Since typical eddy current probes have very low capacitance, the capacitive reactance component can be ignored. The resistance and the inductive reactance ("reactance") components of the impedance are out of phase, so the impedance is the vector sum of the resistance and reactance components. Typically, impedance measurements obtained from eddy current probes are displayed as an impedance plane plot, which is a graph with resistance on the x-axis and the reactance on the y-axis.

Specialized eddy current coating thickness gages that operate on this principle and display the thickness of a coating on an LCD screen are available to measure the thickness of nonconductive coatings on nonmagnetic conductive substrates. These gages use internal calibration curves to correlate the measured impedance magnitudes to a thickness value. If the phase information of the measured impedance is also recorded, thickness of conductive coating on ferromagnetic substrates may be obtained as well. A more versatile eddy current flaw detector may also be used to measure coating thickness using calibration specimens. The calibration specimens are used to establish calibration curves that plot the variation of the instruments response to coating thickness. The instruments response to a sample having an unknown coating thickness is then obtained using the calibration curve. Common practices of eddy current based coating thickness measurement are described in ASTM B244 standards for nonconductive coatings on nonmagnetic substrates. Another method utilizing an eddy current flaw detector for coating thickness measurement is described in U.S. Pat. No. 6,762,604 B2 issued to Le ("the '604 patent"). In the method of '604 patent, an eddy current monitoring system is used to measure the thickness of a coating on a semiconductor wafer using calibration curves. While the method of ASTM B244 and the '604 patent may be suitable to measure the thickness of a coating on a substrate having a constant conductivity, it may not be suitable to measure the thickness of a coating when the conductivity of the substrate changes due to the deposition process.

The disclosed method of thickness measurement is directed to overcoming one or more of the problems set forth above.

SUMMARY

In one aspect, a method of configuring an eddy current detector to measure a thickness of a coating on a conductive substrate is disclosed. The eddy current detector may be adapted to measure impedance of the coated substrate. The impedance may include an inductive reactance component and a resistance component. The method may include establishing an impedance plane plot using a computer. The impedance plane plot may indicate a variation of the impedance of the coated substrate as a function of working frequency, coating thickness, coating electrical conductivity and substrate electrical conductivity. The method may include determining a rotation angle. The rotation angle may be an angle of rotation of the impedance plane plot that will make the inductive reactance component of the impedance substantially insensitive to substrate electrical conductivity within a coating thickness range. The method may further include establishing a calibration curve that is substantially insensitive to substrate electrical conductivity using the rotation angle. The calibration curve may be a curve that relates the inductive reactance component of the impedance to coating thickness.

In another aspect, a method of configuring an eddy current flaw detector to determine if a thickness of a coating on a substrate is within an upper limit and a lower limit is disclosed. The electrical conductivity of the substrate may vary as a function of the coating thickness. The method may include measuring an impedance of a coated substrate using the detector. The impedance may include an inductive reactance component and a resistance component. The method may include determining a rotation angle. The rotation angle may be an angle of rotation of the impedance that makes the inductive reactance component of the impedance substantially insensitive to the electrical conductivity of the substrate within the upper limit and the lower limit of coating thickness. The method may also include inputting the rotation angle into the eddy current flaw detector to adjust the measured impedance. The method may also include establishing a window on the eddy current flaw detector using the measured impedance. An upper end of the window may be representative of the upper limit of thickness and the lower end of the window may be representative of the lower limit of thickness. The method may further include monitoring the measured impedance using the window.

In yet another aspect, a method of measuring a thickness of a coating on a substrate using an eddy current detector is disclosed. The eddy current detector may be configured to measure an impedance of the coated substrate. The impedance may include an inductive reactance component and a resistance component. The electrical conductivity of the substrate may varying as a function of the coating thickness. The method may include determining a rotation angle using a computer modeling approach or use a limited number of calibration blocks with known coating thickness and substrate conductivity. The rotation angle may be an angle of rotation of the impedance that will make the inductive reactance component of the impedance substantially insensitive to the electrical conductivity of the substrate within a range of coating thickness. The method may also include establishing a calibration curve using the computer or calibration blocks with the determined rotation angle to relate coating thickness to the inductive reactance component of the impedance. The method may further include determining the thickness of the coating on the coated substrate by comparing the inductive reactance component of a measured impedance of the coated substrate with the calibration curve.

In a further embodiment, a system to measure a thickness of a coating on a substrate, is disclosed. The system includes an eddy current detector adapted to measure impedance of the coating on the substrate. The impedance includes an inductive reactance component and a resistance component. The system also includes a computer. The computer may be configured to establish an impedance plane plot. The impedance plane plot may indicate a variation of the impedance of the coating on the substrate as a function of coating thickness and substrate electrical conductivity. The computer may also be configured to determine a rotation angle. The rotation angle may be an angle of rotation of the impedance plane plot that will make the inductive reactance component of the impedance substantially insensitive to substrate electrical conductivity within a coating thickness range. The computer may further be configured to establish a calibration curve that is substantially insensitive to substrate electrical conductivity using the rotation angle. The calibration curve may be a curve that relates the inductive reactance component of the impedance to coating thickness.

BRIEF DESCRIPTION OF THE DRAWINGS

FIG. 7 is an illustration of an exemplary eddy current flaw detector used as coating thickness monitor.

DETAILED DESCRIPTION

Figure 1:
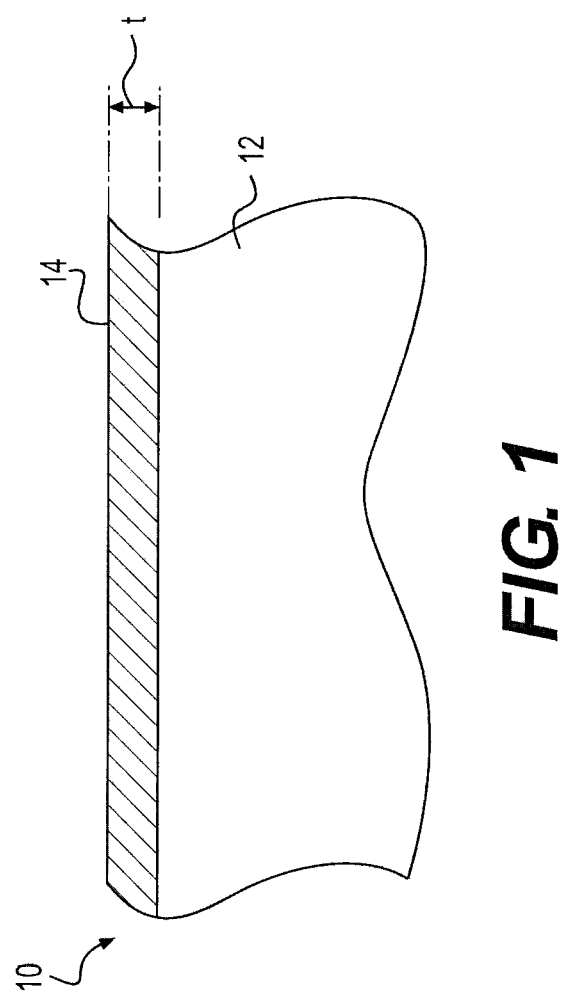
FIG. 1 is an illustration of an exemplary coated component.

FIG. 1 illustrates a portion of a component 10 having a coating 14 applied to a conductive substrate 12. The component 10 may be any part with a coating 14 having a thickness "t" deposited thereon. For instance, component 10 may be a coupling or a fall pipe used in underwater dredging applications, or another part used in an industrial application. Substrate 12 may include any electrically conductive material, such as for example, copper, aluminum, silver, lead, tin, their alloys, etc. Coating 14 may include any non-magnetic material (conductive or non-conductive) applied to substrate 12 by any means. For instance, in some embodiments, coating 14 may be thermally sprayed using HVOF (High Velocity Oxygen Fuel), or another suitable technique on an aluminum alloy substrate.

After depositing coating 14 on substrate 12, an eddy current probe may be used to non-destructively measure the impedance of the coated substrate. Any commercially available eddy current probe may be used to measure the impedance of the coated substrate. The measured impedance value changes with the thickness of coating 14. Previously established calibration curves may be used to determine the thickness of the deposited coating 14 from the measured impedance value. Calibration curves are curves that plot the variation of impedance with coating thickness. In the current disclosure, the reference to curves that plot data describe both figures that graphically represent the relationship between two variables, and a formula that describe a mathematical relationship between the two variables. From a previously established calibration curve, the thickness of a deposited coating 14 may be determined from a measured impedance value using known techniques (extrapolation, interpolation, curve fitting, etc.). The calibration curves may be established either experimentally or by numerical modeling. To establish a calibration curve experimentally, coatings 14 having different thicknesses are deposited (typically using the same coating process) on substantially similar substrates 12, and their impedance measurements obtained using the eddy current probe. A calibration curve may also be obtained by numerical simulations techniques, such as, for example, finite element based techniques. While such calibration curves (discussed above) provide relatively error free thickness measurements when the substrate 12 and the coating 14 electrical conductivity remains a constant, for the reasons discussed previously, errors may be introduced when the substrate 12 and/or coating 14 electrical conductivity changes during the deposition of the coating 14.

Figure 2:
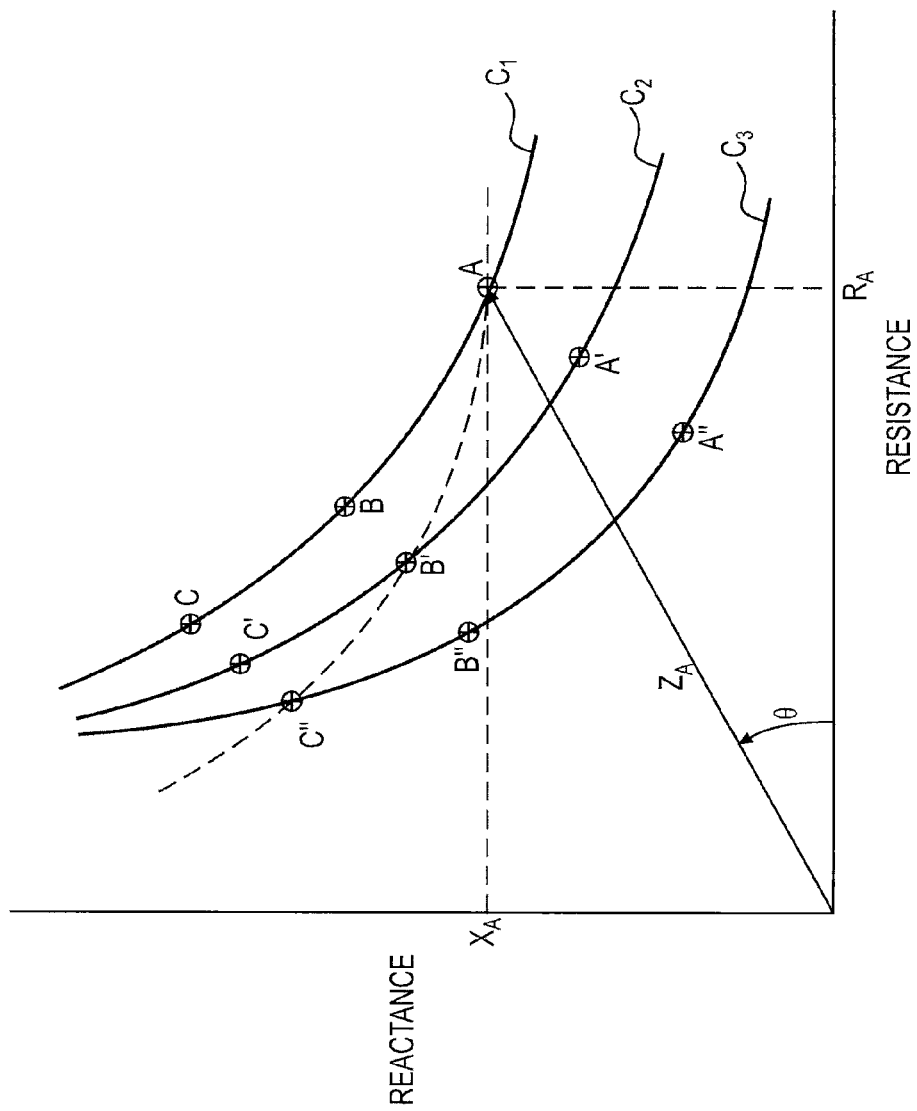
FIG. 2 is an illustration of an exemplary impedance plane plot of the component of FIG. 1.

As discussed in the background section, an impedance value measured by an eddy current probe includes two main components, resistance and reactance, that may be represented in an impedance plane plot. FIG. 2 is a schematic illustration of an exemplary impedance plane plot of coatings 14 having different thicknesses on substrates 12 having different electrical conductivities ("conductivities"). In FIG. 2, curve $C_1$ represents the variation of impedance values with thickness of the coating 14 on a substrate 12 having a constant conductivity $K_1$. Similarly curves $C_2$ and $C_3$ represent the variation of impedance values with coating 14 thickness on substrates 12 having constant conductivities of $K_2$ and $K_3$, respectively. The data plotted in FIG. 2 may be experimentally measured using an eddy current probe or may be obtained using numerical simulations. As discussed in the background section, the impedance value $Z_A$ at location A includes a resistance component $R_A$ and a reactance component $X_A$. The reactance component $X_A$ is out of phase with the resistance component $R_A$ by an angle $\theta$. The magnitude $Z_A$ is related to the reactance and resistance components $X_A$ and $R_A$ as $\sqrt{(X_A^2 + R_A^2)}$, and the phase difference $\theta$ between the reactance and resistance components $X_A$ and $R_A$ is arctan $(X_A/R_A)$.

In the impedance plane plot of FIG. 2, points A, B, and C represent the impedance values at coating thicknesses $t_A$, $t_B$, and $t_C$ on a substrate having conductivity $K_1$. Points A', B', and C' represent the impedance values at coating thicknesses $t_A$, $t_B$, and $t_C$ on a substrate having conductivity $K_2$, and points A", B", and C" represent the impedance values at coating thicknesses $t_A$, $t_B$, and $t_C$ on a substrate having conductivity $K_3$. If the conductivity of the substrate 12 remains a constant as the thickness of the coating 14 changes from $t_A$ to $t_B$ to $t_C$, one of curves $C_1$, $C_2$, and $C_3$ may be used as a calibration curve to determine the coating thickness based on the value of the substrate conductivity. That is, curve $C_1$ may be used as the calibration curve to determine coating thickness if the substrate conductivity remains constant at $K_1$. And, curves $C_2$ and $C_3$ may be used as the calibration curve if the substrate conductivity remains constant at $K_2$ and $K_3$, respectively. However, in some cases, high temperature coating deposition techniques, such as thermal spraying, may change the conductivity of the substrate 12 and/or the coating 14 during the deposition process. Since the effect of changing coating 14 conductivity is small compared to that of substrate 12 conductivity, for the sake of brevity, only the effect of changing substrate 12 conductivity is discussed below.

Due to the change in substrate conductivity as a result of the high temperature deposition process, the conductivity of the substrate 12 may change from $K_1$ when the coating thickness is $t_A$, to $K_2$ when the coating thickness is $t_B$, and to $K_3$ when the coating thickness is $t_C$. Therefore, as a result of the change in substrate conductivity, the measured impedance values at coating thickness $t_A$, $t_B$, and $t_C$ may be A, B', C", respectively. As discussed above, changing coating 14 conductivity during the deposition process may also affect the measured impedance values in a manner similar to that discussed above. Since the change in substrate conductivity with coating thicknesses is not known, determining coating thickness using constant conductivity calibration curves (such as, curves $C_1$, $C_2$, and $C_3$) may be error-prone. The method described in the instant application minimizes this error by accounting for the variation in substrate and/or coating conductivity in the calibration curves.

Figure 3:
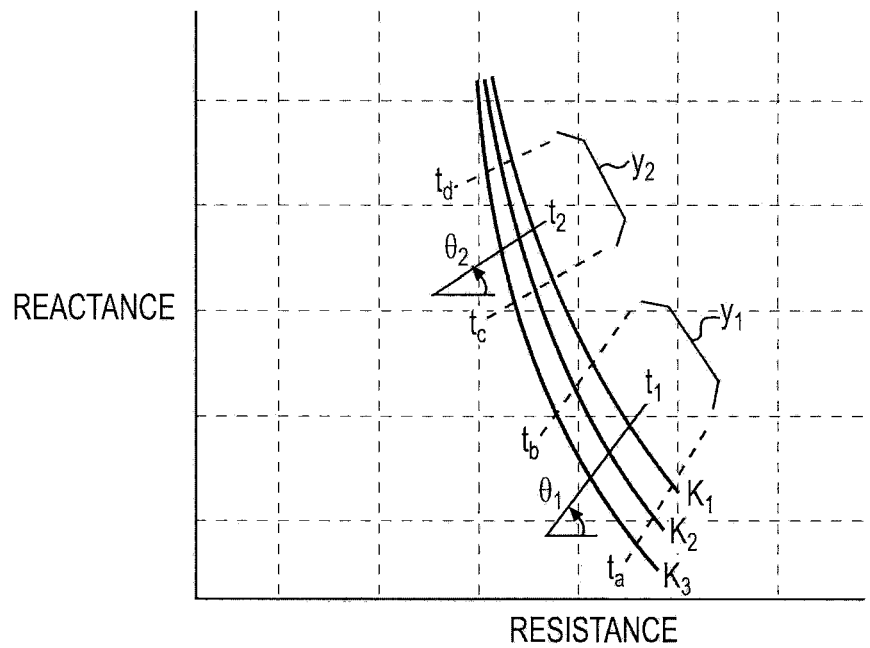
FIG. 3 is an illustration of an exemplary impedance plane plot showing the variation of impedance values with coating thickness and substrate conductivity.

FIG. 3 is an illustration of an exemplary impedance plane plot showing the variation of impedance values with coating 14 thickness and substrate 12 conductivity. In FIG. 3, lines $t_1$ and $t_2$ represent lines of constant thickness, and curves $K_1$, $K_2$, and $K_3$ represent curves of constant substrate 12 conductivity. That is, points along lines $t_1$ represent impedance values of coatings 14 having the same thickness $t_1$ deposited on substrates 12 having different conductivities, and points on curve $K_1$ represent impedance values of coatings 14 having different thicknesses deposited on a substrate 12 having the same conductivity $K_1$. Similarly, points along lines $t_2$ represent impedance values of coatings 14 having a thickness $t_2$ deposited on substrates having different conductivities. And, points along curves $K_2$ and $K_3$ represent impedance values of coatings having different thicknesses on substrates 12 having conductivities $K_1$ and $K_2$, respectively. As evident from FIG. 3, segments of curves $K_1$, $K_2$, and $K_3$ are approximately parallel to each other. For instance, a segment $Y_1$ of the curves $K_1$, $K_2$, and $K_3$ between constant thickness lines $t_a$ and $t_b$ are approximately parallel to each other, and a segment $Y_2$ of these curves between constant thickness lines $t_c$ and $t_d$ are approximately parallel to each other. Since the curves $K_1$, $K_2$, and $K_3$ are approximately parallel to each other between constant thickness lines $t_a$ and $t_b$, the constant thickness lines between $t_a$ and $t_b$ may also be approximately parallel to each other. Similarly, the constant thickness lines may also be approximately parallel to each other between $t_c$ and $t_d$.

Figure 4:
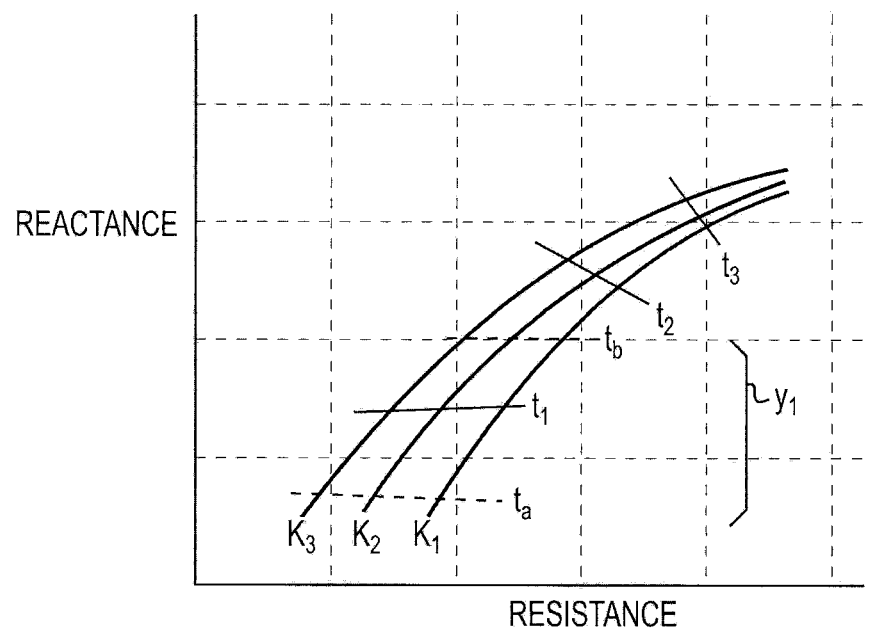
FIG. 4 is an illustration of the impedance plane plot of FIG. 3 rotated by an angle $\theta_1$.

By rotating the impedance curves by an angle $-\theta_1$, the constant thickness lines in segment $Y_1$ (that is, between $t_a$ and $t_b$) may be made parallel to the x-axis. FIG. 4 is an illustration of the impedance plane plot of FIG. 3 rotated by an angle $-\theta_1$. The effect of the rotation is to minimize, or eliminate, the impact of substrate conductivity on the reactance component of the impedance in segment $Y_1$. That is, within segment $Y_1$ of FIG. 4, the change in substrate conductivity (for example, between $K_1$ and $K_3$) does not affect the reactance component of the measured impedance value. Therefore, for coating thickness measurements between $t_a$ and $t_b$, after rotation by an angle $-\theta_1$, only the change in the reactance component of the impedance value is necessary to the measure coating thickness.

Figure 5:
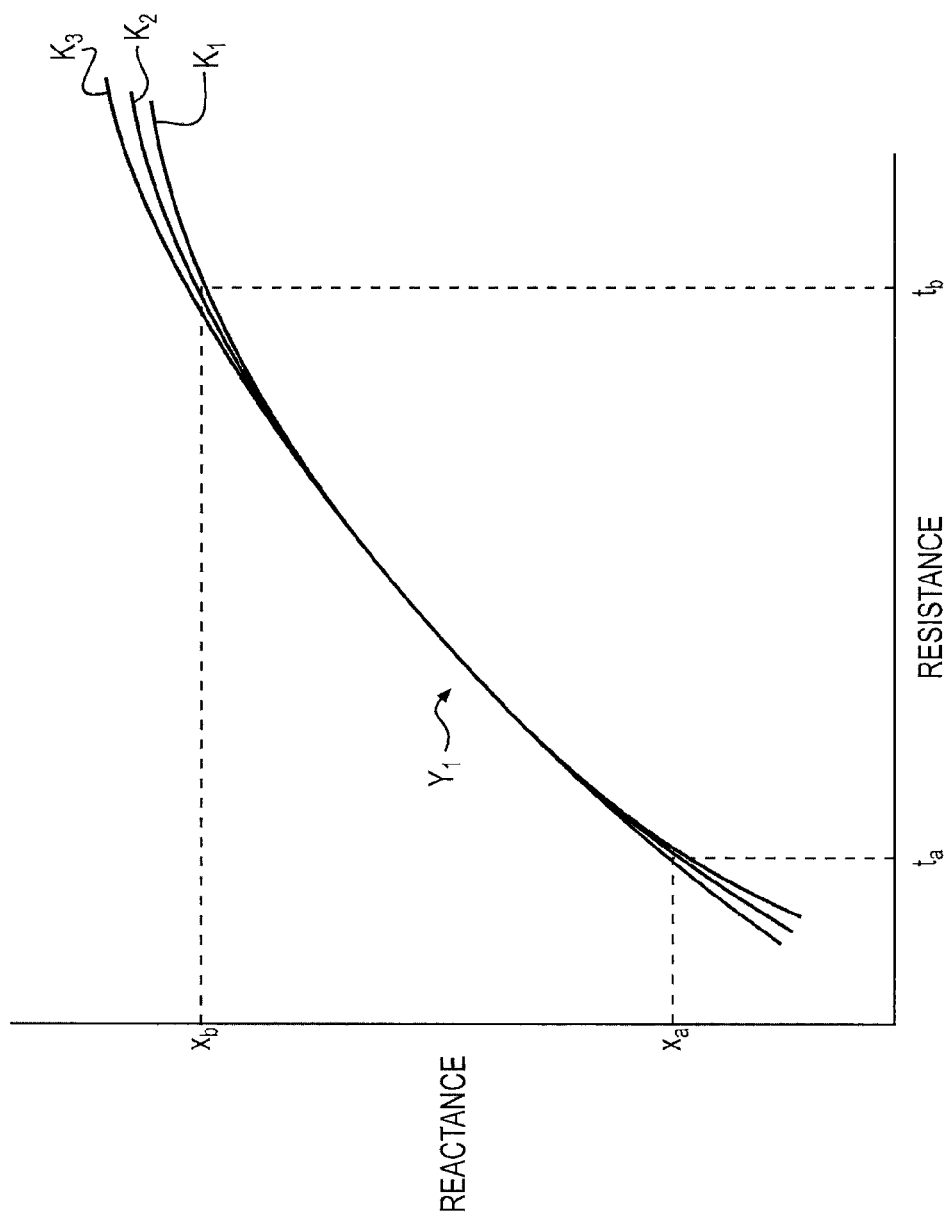
FIG. 5 is an illustration of the reactance versus coating thickness in a segment of FIG. 4.

FIG. 5 shows a plot of reactance versus coating thickness in segment $Y_1$ of FIG. 4. Since the reactance component is substantially insensitive to the change in substrate conductivity between $t_a$ and $t_b$, the curves $K_1$, $K_2$, and $K_3$ overlap in this region. Outside of the thickness range $t_a$ and $t_b$, the curves $K_1$, $K_2$, and $K_3$ begin to diverge. Therefore, the error induced due to the variation in coating conductivity may be minimized, or even eliminated, by using FIG. 5 as a calibration curve to measure the coating thickness in segment $Y_1$. For measurement of coating thickness outside of segment $Y_1$ (such as, for example, in segment $Y_2$ of FIG. 3), the impedance plane plot may have to be rotated by a different angle (such as, for example, $\theta_2$ of FIG. 3) and a different calibration curve (similar to FIG. 5) generated. Therefore, by rotating the impedance plane plot by an appropriate angle, a calibration curve that is substantially insensitive to the substrate conductivity within any coating thickness range may be obtained. Such a calibration curve may be used to correlate the measured impedance values to coating thickness values when the substrate and/or coating conductivity changes during the deposition process. Although the change in substrate conductivity is described as being a result of the deposition process, this is not a limitation. The disclosed techniques may be applied to minimize the measurement error in any application where the substrate conductivity changes, for any reason, between two thickness measurements. Although, in the description above, the effect of substrate conductivity on the reactance component of the impedance is minimized by rotation of the impedance plane plot by an angle $\theta$, a person of ordinary skill in the art would recognize that a similar result may also be obtained by rotating the impedance plane plot by a different angle (such as, for example, $\theta \pm 90°$) to minimize the effect of substrate conductivity on the resistance component of the impedance. Additionally, a computer may be used to carry out the steps described herein. In case of nonconductive or poorly conductive coating 12, the curvatures of impedance curve $K_1$, $K_2$ and $K_3$ may be smaller compared to those of highly conductive coatings. Thus, a single rotation angle $\theta_1$ may be suitable to a larger segment of impedance curve, like $Y_1$, or a larger variation of substrate conductivities. In another way, less number of rotation angles is needed to achieve required accuracies throughout the interested coating thickness range.

INDUSTRIAL APPLICABILITY

The disclosed eddy current based method of measuring the thickness of a coating may be applicable to measure the coating thickness in any application. The disclosed technique may be especially useful to measure the coating thickness in an application where the substrate and/or coating electrical conductivity changes between thickness measurements. The disclosed methods may minimize the effect of the substrate and/or coating conductivity on one of the components of the measured impedance by rotation of the impedance plane plot by a suitable rotation angle.

Figure 6:
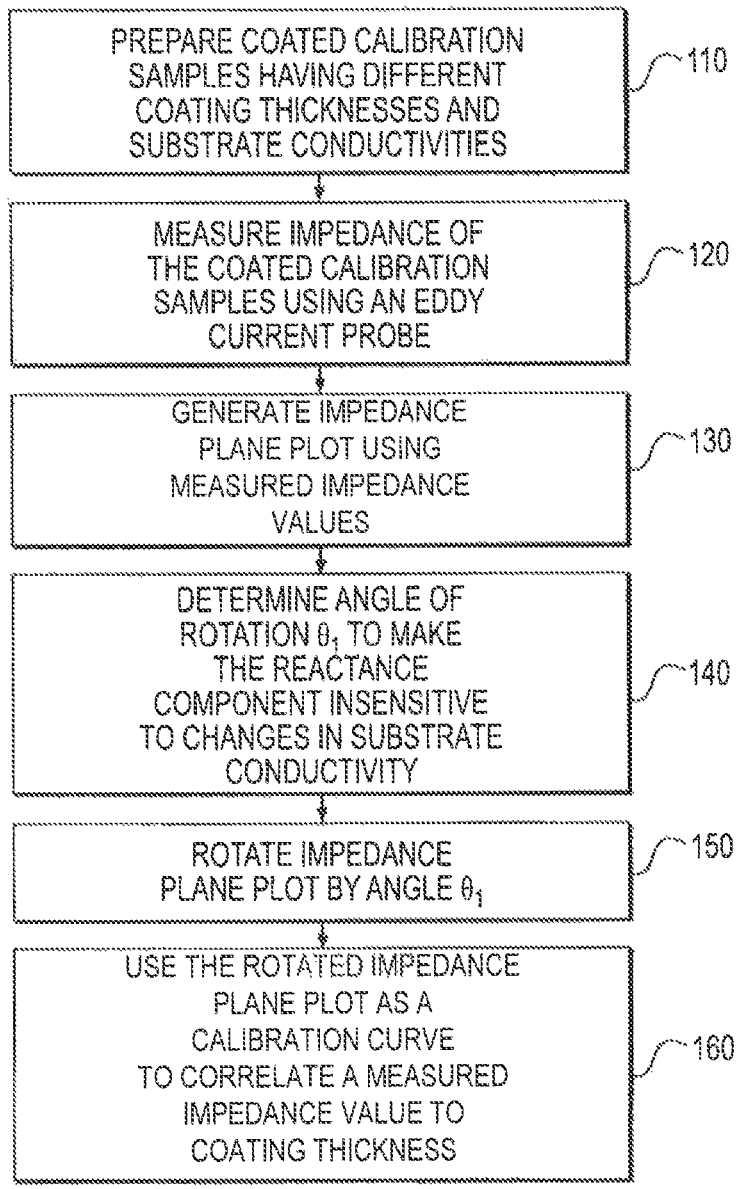
FIG. 6 is a flow chart of an exemplary method of determining rotation angle $\theta 1$.

The rotation angle for any coating thickness range (such as, for example, $\theta_1$ for a thickness range between $t_a$ and $t_b$, and $\theta_2$ for a thickness range between $t_c$ and $t_d$) may be obtained by experimentation or by numerical simulation (such as, for example, on a computer). FIG. 6 is a flow chart illustrating an exemplary experimental method of determining the rotation angles for different coating thickness ranges. To experimentally determine the rotation angles, coated substrates having a range of coating thicknesses and substrate conductivities may be prepared and used as calibration samples (step 110). To reduce variability, the coating may be deposited on each of the calibration samples using the same coating technique. An eddy current probe may then be used to measure the impedance value of each of the calibration samples (step 120). An impedance plane plot (similar to FIG. 3) may then be generated using the measured impedance values (step 130). The generation of the impedance plane plot may be performed manually or by using a computer. Although a plot is described as being generated, in some embodiments, a graphical plot may not be generated. Instead, the measured data may be input into known computer programs (such as, for example, Excel by Microsoft®, Matlab by MathWorks®) determine the mathematical relationship between the measured values. The rotation angle to make the reactance component of the measured impedance substantially insensitive to changes in substrate conductivity for a desired thickness range is then obtained (step 140). For example, it may be known that the expected coating thickness in an application may be between $t_a$ and $t_b$. Based on this prior knowledge of expected coating thickness range, as explained with reference to FIG. 3, the rotation angle $\theta_1$ which will make the measured impedance values of substrates having the same coating thickness and different conductivities be substantially the same within the thickness range $t_a$ and $t_b$, may be determined. The impedance plane plot may then be rotated by this rotation angle $\theta_1$ as explained with reference to FIG. 4 (step 150) to obtain a calibration curve as described with reference to FIG. 5. The calibration curve may then be used to correlate a measured impedance value to coating thickness (step 160). The determination of the rotation angle and the rotation of impedance plane plot by this angle may be performed manually, or by using a computer program.

In embodiments where a computer program is used, the measured impedance values may be input into the program to determine the rotation angle $\theta_1$ to make the reactance component substantially insensitive to substrate conductivity. In these embodiments, the computer program may also be configured to rotate the impedance plane plot by the rotation angle $\theta_1$, and translate a measured impedance value to a coating thickness after the rotation. In some embodiments, instead of experimentally measuring impedance values on calibration samples (step 110), numerical simulations may be used to determine the impedance values of coatings of different thicknesses on different conductivity substrates. These numerically obtained impedance values may be used to obtain the desired rotation angle $\theta_1$. The computer program may also be configured to use this rotation angle $\theta_1$ to correct a measured impedance value, and translate the corrected impedance value to a coating thickness. The testing frequency of instrument/probe may be carefully selected to minimize thickness measurement errors and/or to simplify the calibration process.

In some embodiments, the determined rotation angle $\theta_1$ may be used with a commercially available eddy current flaw detector to convert the flaw detector into a go/no-go coating thickness monitor. Such a thickness monitor may be used to quickly verify whether the thickness of a coating on a substrate is within acceptable limits (such as, for example, within limits $t'_a$ and $t'_b$). An exemplary process of using a commercially available eddy current flaw detector as a go/no-go thickness monitor is described below with reference to FIG. 7.

FIG. 7 illustrates an exemplary eddy current flaw detector (detector 20) used to measure the impedance of a coating 14 on a substrate 12. Detector 20 may include a display 22, and may be used along with an eddy current probe (probe 24). Any known eddy current flaw detector (such as, for example, Olympus Nortec 500D) and probe (such as, for example, Nortec P/N 9222420) may be used as detector 20 and probe 24, respectively. Detector 20 may include knobs 28 and buttons 32 for adjusting parameters, such as signal frequency, signal gain, horizontal and vertical location of a measurement on display 22, rotation angle, etc. may be input and/or be adjusted. The frequency of the detector 20 may be adjusted to match the frequency of the probe 20, and the rotation angle $\theta_1$ for a thickness range $t_a$ to $t_b$ ($t_a \leq t'_a$ and $t_b \geq t'_b$) may then be input into detector 20 using the knobs 28 and buttons 32. Calibration samples having coatings of different thicknesses may then be used to define a measurement box 34 that is representative of the acceptable coating thickness range $t'_a$ to $t'_b$ on display 22. The lower end 34a of the measurement box 34 may be adjusted to coincide with the lower end of the acceptable thickness range $t'_a$ by measuring the impedance of a calibration sample having a coating thickness of $t'_a$, and adjusting the vertical position of the observed reading on display 22 to coincide with the lower end 34a of box 34. The upper end 34b of the measurement box 34 may similarly be defined to be representative of the upper end of the acceptable thickness range $t'_b$. Impedance measurements that falls within the upper and the lower ends 34b, 34a of the measurement box 34 are indicative of coatings 14 having an acceptable thickness (between $t'_a$ and $t'_b$).

Minimizing the error induced in the coating thickness measurement due to substrate conductivity enables an eddy current probe to be used to measure the coating thickness on a variable conductivity substrate. The error is minimized by determining a rotation angle that makes one of the components of the measured impedance substantially insensitive to substrate conductivity, and rotating the calibration curve of the eddy current probe by the determined angle.

It will be apparent to those skilled in the art that various modifications and variations can be made to the disclosed eddy current based method of measuring the thickness of a coating. Other embodiments will be apparent to those skilled in the art from consideration of the specification and practice of the disclosed method. It is intended that the specification and examples be considered as exemplary only, with a true scope being indicated by the following claims and their equivalents.

What is claimed is:

1. A method, comprising:
configuring an eddy current detector to measure a thickness of a coating on a substrate, the eddy current detector being adapted to measure impedance of the coated substrate, the impedance including an inductive reactance component and a resistance component;
establishing an impedance plane plot using a computer, the impedance plane plot indicating a variation of the impedance of the coated substrate as a function of coating thickness and substrate electrical conductivity;
determining a rotation angle, the rotation angle being an angle of rotation of the impedance plane plot that will make the inductive reactance component of the impedance substantially insensitive to substrate electrical conductivity within a coating thickness range such that a change in the substrate electrical conductivity does not affect the inductive reactance component of the measured impedance within the coating thickness range;
establishing, using the computer, a calibration curve that is substantially insensitive to substrate electrical conductivity using the rotation angle, the calibration curve being a curve that relates the inductive reactance component of the impedance to coating thickness; and reconfiguring the eddy current detector with the calibration curve to enable the eddy current detector to correlate the measured impedance of the coated substrate with the thickness of the coating within the coating thickness range using the calibration curve regardless of the change in the substrate electrical conductivity.

2. The method of claim 1, wherein establishing the impedance plane plot includes determining the impedance using numerical simulation.

3. The method of claim 1, wherein establishing the impedance plane plot includes determining the impedance using experimental measurements on calibration samples.

4. The method of claim 1, wherein establishing the impedance plane plot includes measuring the impedance on multiple calibration samples having varying coating thicknesses and varying substrate electrical conductivities.

5. The method of claim 1, further including rotating the impedance plane plot by the rotation angle to make the inductive reactance components of the impedance be substantially the same at different substrate electrical conductivities.

6. The method of claim 1, wherein the inductive reactance component of the impedance varies as a function of coating thickness.

7. The method of claim 1, further including correlating a measured impedance value of the coating to a thickness using the calibration curve.

8. The method of claim 1, further including depositing the coating on the substrate using a thermal spraying process.

9. The method of claim 1, further including depositing the coating on the substrate using a high velocity oxygen fuel process.

10. A method of configuring an eddy current flaw detector to determine if a thickness of a coating on a substrate is within an upper limit and a lower limit, the electrical conductivity of the substrate varying as a function of the coating thickness, comprising:

measuring an impedance of a coated substrate using the detector, the impedance including an inductive reactance component and a resistance component;

determining a rotation angle, the rotation angle being an angle of rotation of the impedance that makes the inductive reactance component of the impedance substantially insensitive to the electrical conductivity of the substrate within the upper limit and the lower limit of coating thickness such that a change in the electrical conductivity of the substrate does not affect the inductive reactance component of the measured impedance within the upper limit and the lower limit;

inputting the rotation angle into the eddy current flaw detector to reconfigure the eddy current flaw detector with the rotation angle to enable the eddy current flaw detector to adjust the measured impedance;

establishing a window on the eddy current flaw detector using the measured impedance, an upper end of the window being representative of the upper limit of thickness and the lower end of the window being representative of the lower limit of thickness; and monitoring the measured impedance using the window.

11. The method of claim 10, wherein determining the rotation angle includes establishing an impedance plane plot, the impedance plane plot indicating the variation of impedance values as a function of coating thickness and substrate electrical conductivity.

12. The method of claim 11, wherein establishing the impedance plane plot includes experimentally measuring the impedance values using calibration samples.

13. The method of claim 11, wherein establishing the impedance plane plot includes determining the impedance values using numerical simulations.

14. The method of claim 11, wherein the substrate includes aluminum and the coating is deposited on the substrate using thermal spraying.

15. A method of determining a thickness of a coating on a substrate using an eddy current detector configured to measure an impedance of the coated substrate, the impedance including an inductive reactance component and a resistance component, the electrical conductivity of the substrate varying as a function of the coating thickness, comprising:

determining a rotation angle using a computer, the rotation angle being an angle of rotation of the impedance that will make the inductive reactance component of the impedance substantially insensitive to the electrical conductivity of the substrate within a range of coating thickness such that a change in the electrical conductivity of the substrate does not affect the inductive reactance component of the measured impedance within the coating thickness range;

establishing a calibration curve using the computer with the determined rotation angle to relate coating thickness to the inductive reactance component of the impedance; and configuring the eddy current detector with the calibration curve to enable the eddy current detector to determine the thickness of the coating on the coated substrate by comparing the inductive reactance component of a measured impedance of the coated substrate with the calibration curve regardless of the change in the substrate electrical conductivity.

16. The method of claim 15, wherein determining the rotation angle includes establishing an impedance plane plot, the impedance plane plot indicating the variation of impedance values as a function of coating thickness and substrate electrical conductivity.

17. The method of claim 16, wherein establishing the impedance plane plot includes experimentally measuring the impedance values using calibration samples.

18. The method of claim 16, wherein establishing the impedance plane plot includes determining the impedance values using numerical simulations.

19. The method of claim 16, wherein determining the rotation angle includes establishing the rotation angle as an angle by which the impedance plane plot is to be rotated to make the inductive reactance component of the impedance values be substantially the same at different substrate conductivities.

20. The method of claim 15, further including depositing the coating on the substrate using a thermal spraying process.

21. A system to measure a thickness of a coating on a substrate, comprising:

an eddy current detector adapted to measure impedance of the coating on the substrate, the impedance including an inductive reactance component and a resistance component; and a computer configured to;

establish an impedance plane plot, the impedance plane plot indicating a variation of the impedance of the coating on the substrate as a function of coating thickness and substrate electrical conductivity;

determine a rotation angle, the rotation angle being an angle of rotation of the impedance plane plot that will make the inductive reactance component of the impedance substantially insensitive to substrate electrical conductivity within a coating thickness range such that a change in the substrate electrical conductivity does not affect the inductive reactance component of the measured impedance within the coating thickness range; and establish a calibration curve that is substantially insensitive to substrate electrical conductivity using the rotation angle, the calibration curve being a curve that relates the inductive reactance component of the impedance to coating thickness, wherein the eddy current detector is reconfigured with the calibration curve to enable the eddy current detector to correlate the measured impedance of the coated substrate with the thickness of the coating within the coating thickness range using the calibration curve regardless of the change in the substrate electrical conductivity.

22. The system of claim 21 wherein the computer is further configured to correlate a measured impedance value of the coating to a thickness using the calibration curve.

* * * * *